(12) United States Patent
Köhn et al.

(10) Patent No.: US 10,336,716 B2
(45) Date of Patent: Jul. 2, 2019

(54) THERMODYNAMICALLY STABLE CRYSTAL MODIFICATION OF 2-METHYL-N-(5-METHYL-1, 3, 4-OXADIAZOL-2-YL)-3-(METHYLSULFONYL)-4-(TRIFLUOROMETHYL)BENZAMIDE

(71) Applicant: Bayer CropScience Aktiengesellschaft, Monheim am Rhein (DE)

(72) Inventors: Arnim Köhn, Klein-Winternheim (DE); Christopher Hugh Rosinger, Hofheim (DE); Christian Waldraff, Bad Vilbel (DE); Britta Olenik, Bottrop (DE); Birgit Keil, Düsseldorf (DE); Benedikt Mehl, Wuppertal (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/774,200

(22) PCT Filed: Nov. 4, 2016

(86) PCT No.: PCT/EP2016/076620
§ 371 (c)(1),
(2) Date: May 7, 2018

(87) PCT Pub. No.: WO2017/080912
PCT Pub. Date: May 18, 2017

(65) Prior Publication Data
US 2018/0319754 A1    Nov. 8, 2018

(30) Foreign Application Priority Data
Nov. 9, 2015  (EP) ..................... 15193615

(51) Int. Cl.
| A01N 25/12 | (2006.01) |
| A01N 43/82 | (2006.01) |
| C07D 271/113 | (2006.01) |

(52) U.S. Cl.
CPC .......... *C07D 271/113* (2013.01); *A01N 43/82* (2013.01); *C07B 2200/13* (2013.01)

(58) Field of Classification Search
CPC ........................... C07D 271/113; A01N 43/82
See application file for complete search history.

(56) References Cited

U.S. PATENT DOCUMENTS 9,101,141 B2   8/2015  Köhn et al.
2014/0080705 A1   3/2014  Köhn et al.

FOREIGN PATENT DOCUMENTS

EP    1 314 724 A1   5/2003
WO    2012/126932 A1  9/2012

OTHER PUBLICATIONS

McClurg, R.B. X-Ray Powder Diffraction (XRPD) to Describe Crystal Forms. SSCI. Jul. 9, 2008.*
PCT International Search Report for PCT/EP2016/076620, dated Jan. 24, 2017.
Bernstein, et al., "Concomitant Polymorphs," Angew.Chem. Int. Ed., (1999), vol. 38: 3440-3461.

* cited by examiner

*Primary Examiner* — John Pak
(74) *Attorney, Agent, or Firm* — Mcbee Moore Woodward & Vanik IP, LLC

(57) ABSTRACT

A thermodynamically stable crystal modification of 2-methyl-N-(5-methyl-1,3,4-oxadiazol-2-yl)-3-(methylsulfonyl)-4-(trifluoromethyl)benzamide is described. This thermodynamically stable crystal modification has particular advantages in the stability of suspension formulations.

11 Claims, 11 Drawing Sheets

Illustrations
Figure 1: X-ray diffractogram of crystal modification "A"
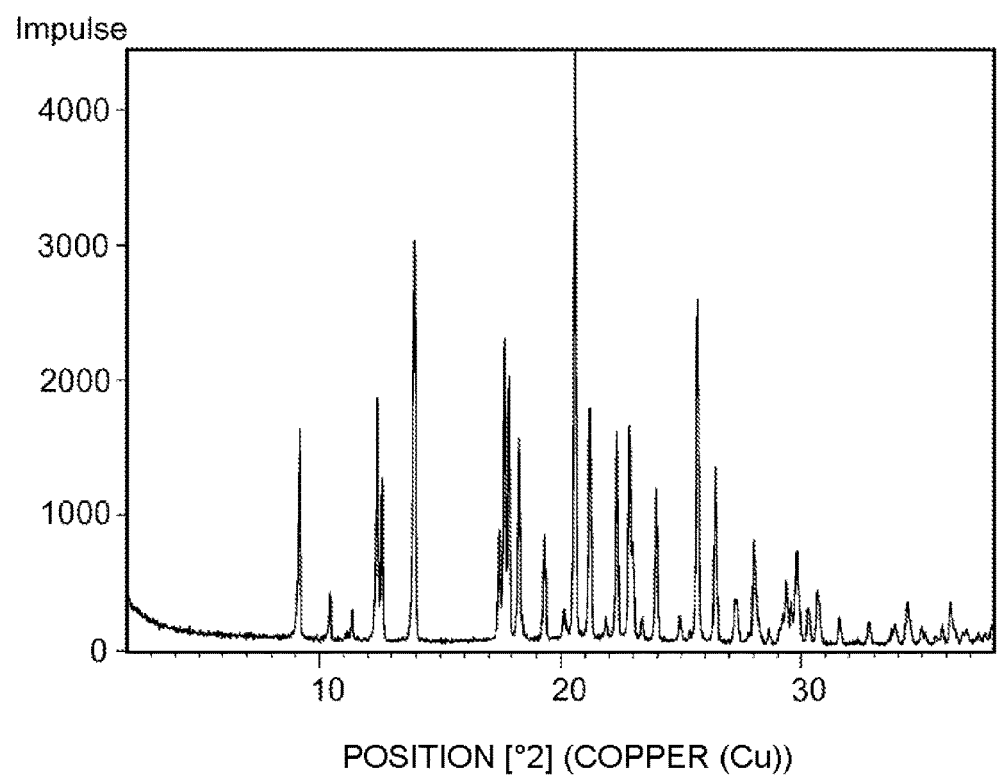

Figure 2: X-ray diffractogram of crystal modification "B"
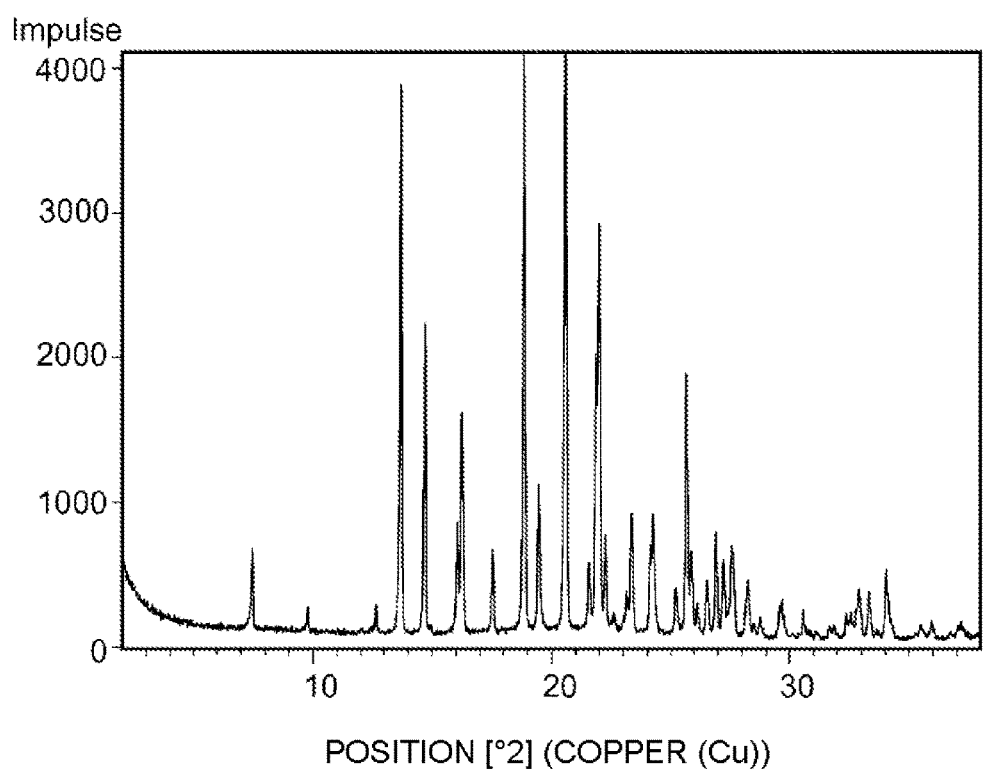

Figure 3: X-ray diffractogram of crystal modification "C"
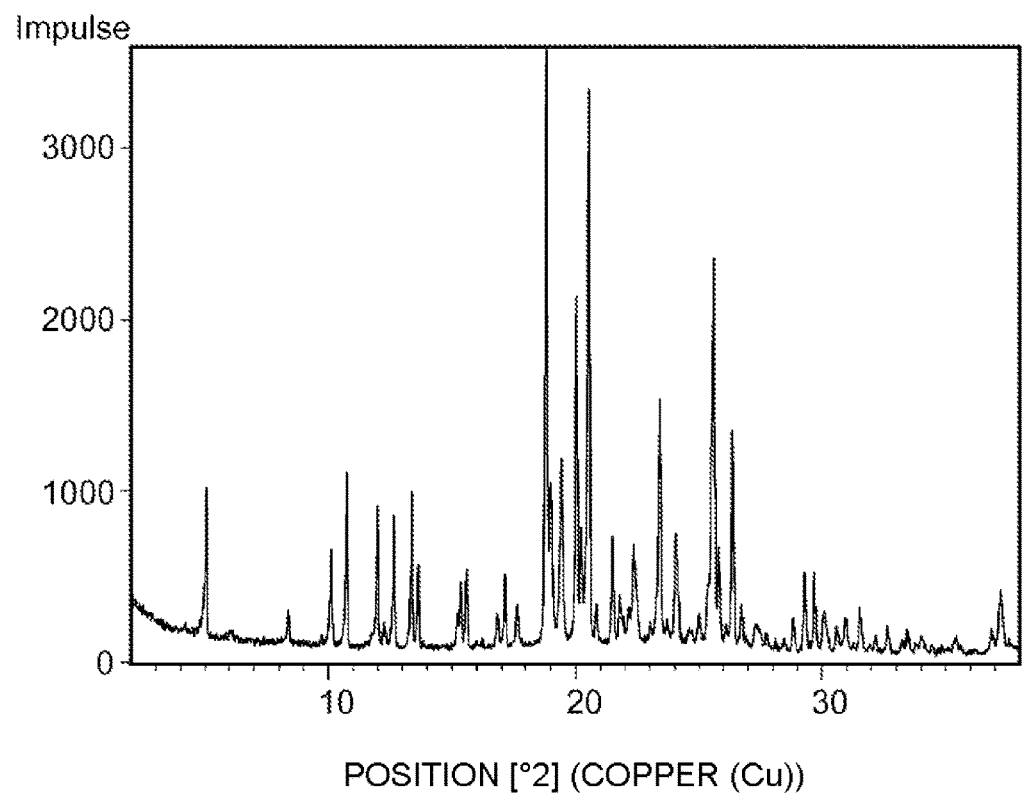

Figure 4: X-ray diffractogram of crystal modification "D"
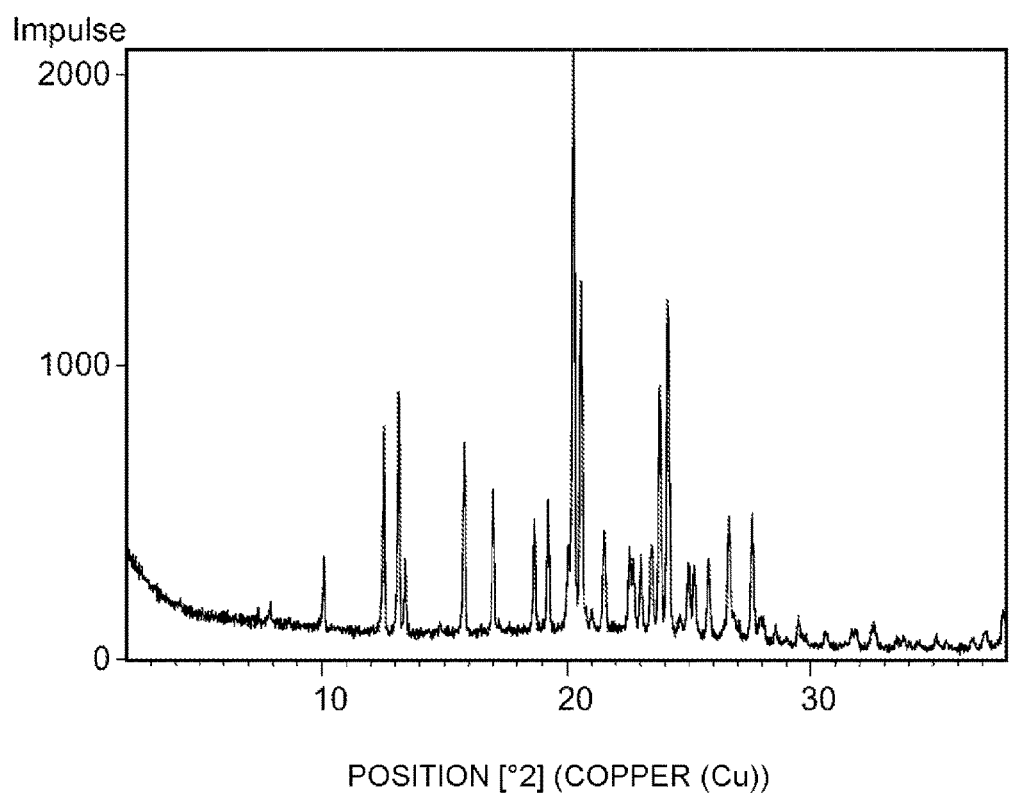

Figure 5: X-ray diffractogram of crystal modification "E"
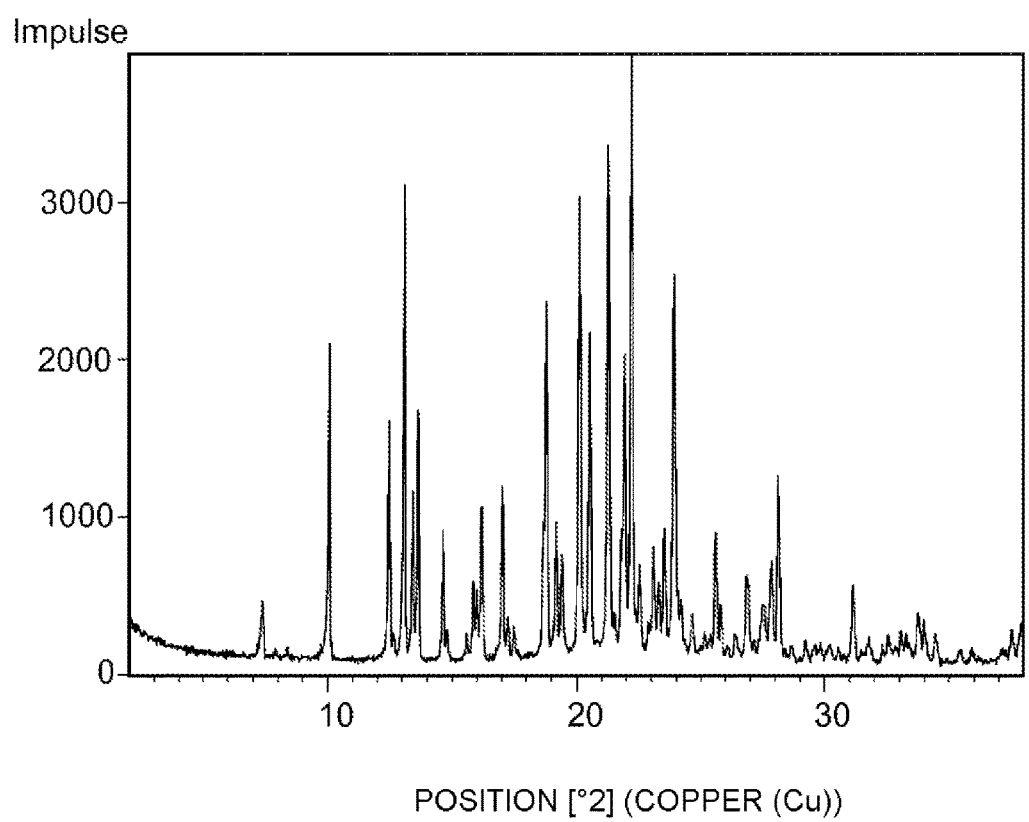

Figure 6: X-ray diffractogram of crystal modification "F"
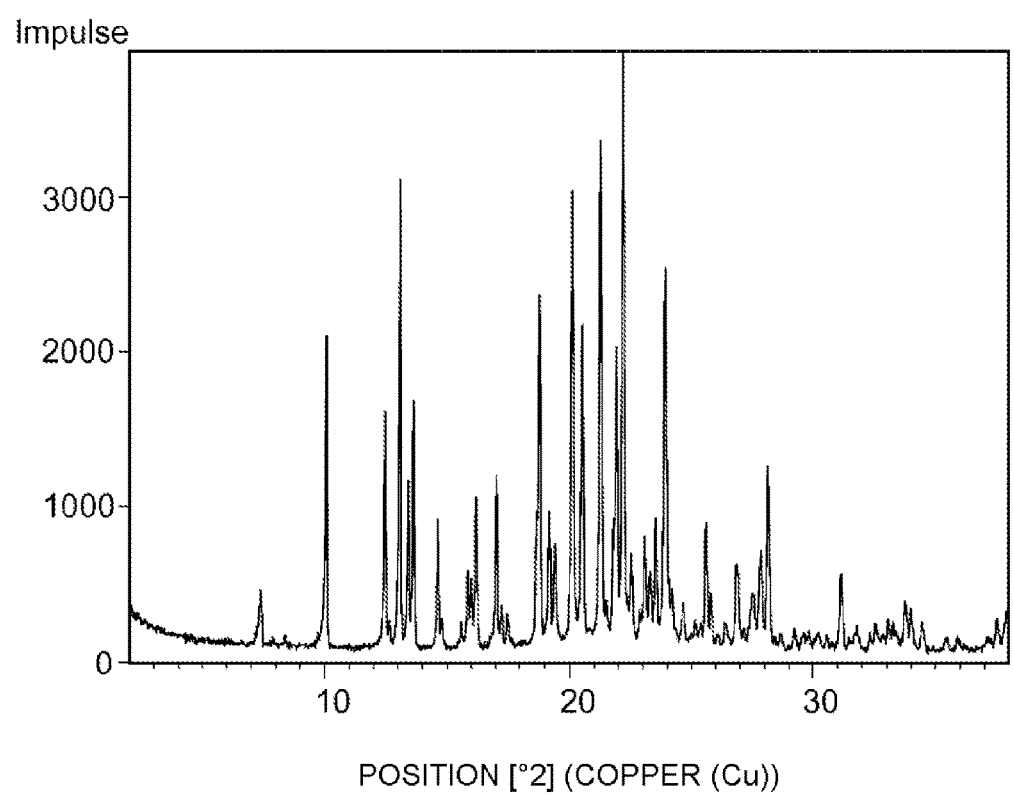

Figure 7: X-ray diffractogram of crystal modification "G"
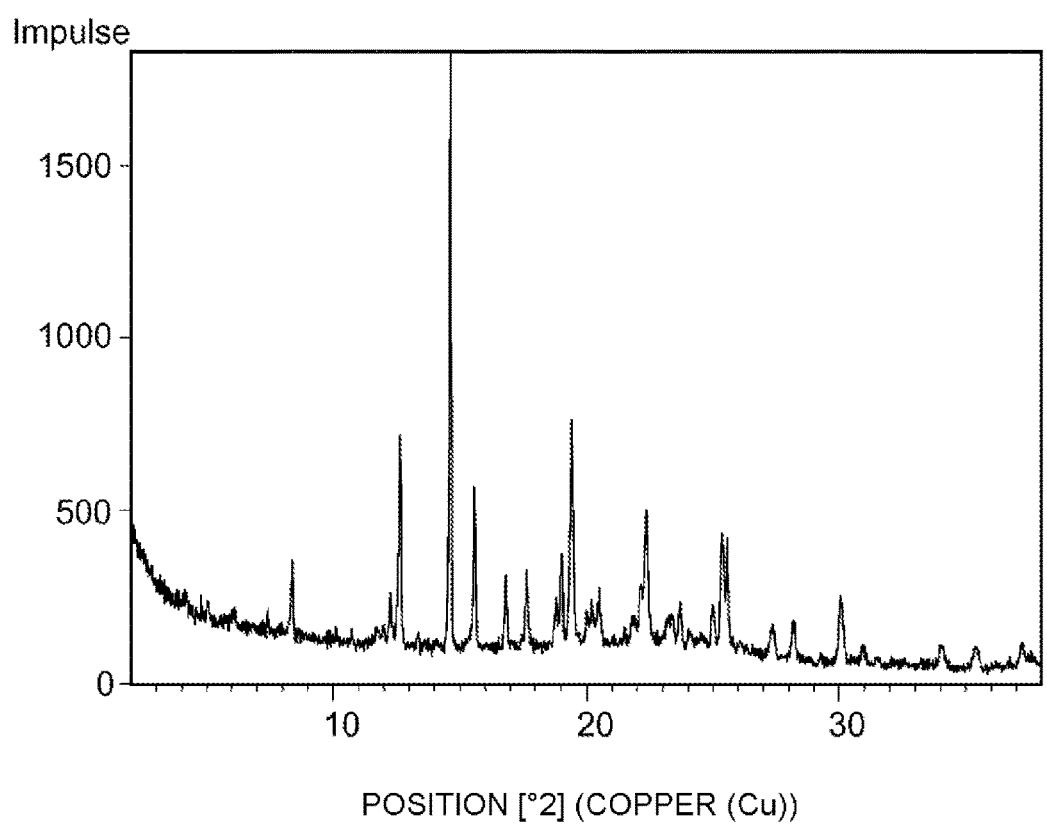

Figure 8: Ramanspectrum of modification "A"
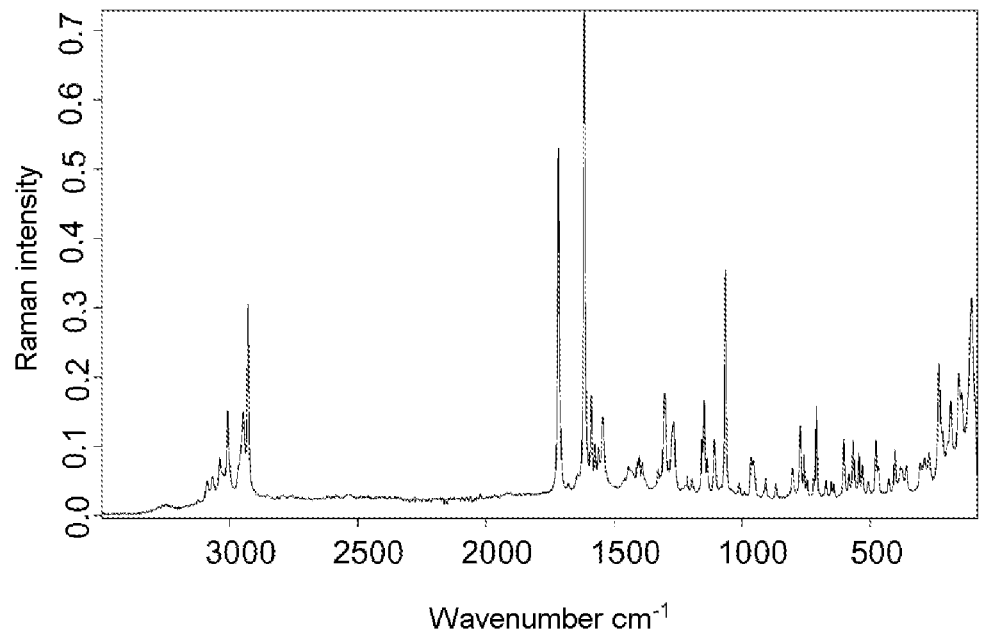
Figure 9: Ramanspectrum of modification "B"
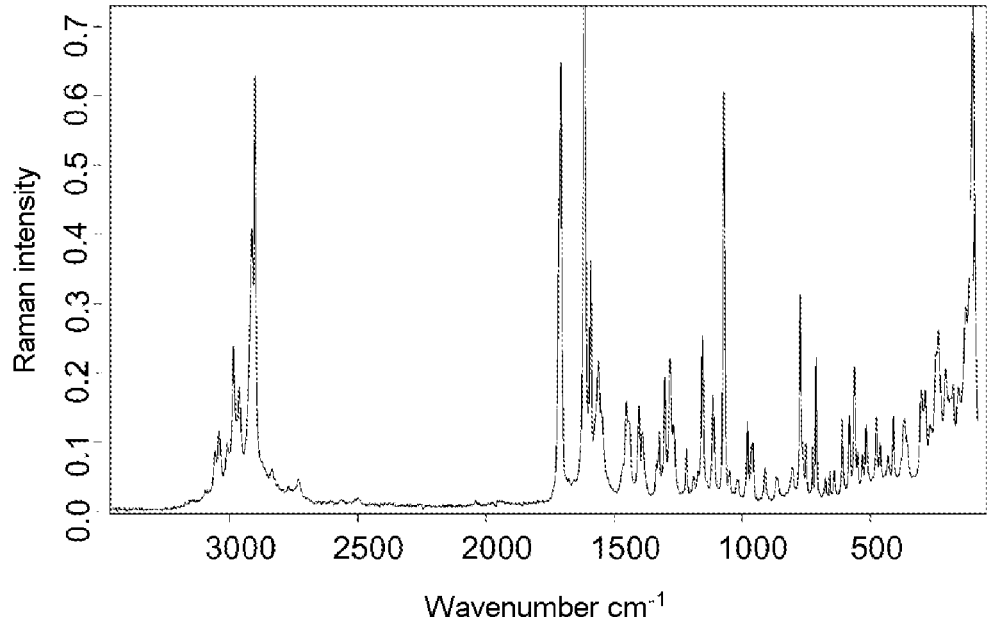

Figure 10: Ramanspectrum of modification "C"
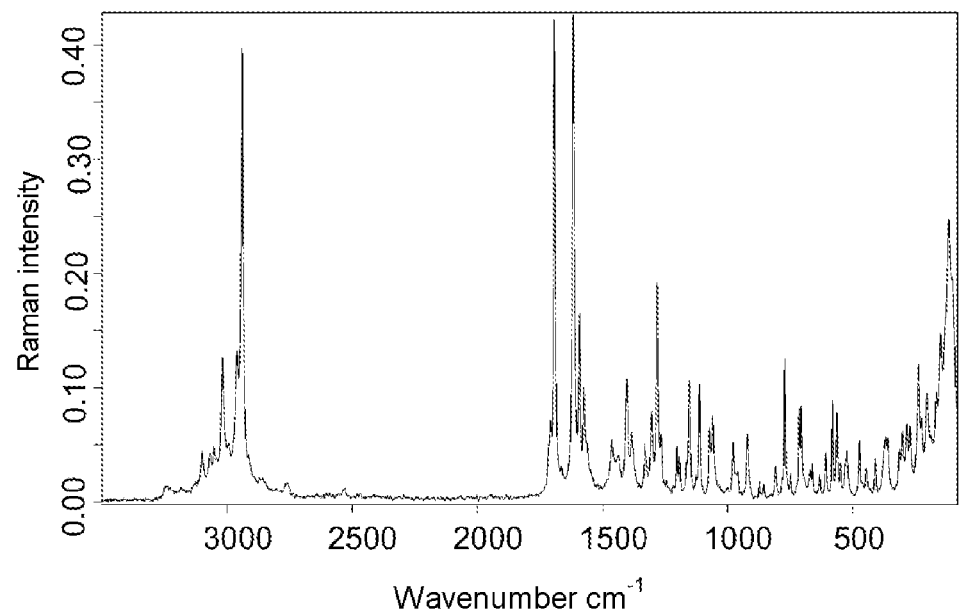
Figure 11: Ramanspectrum of modification "D"
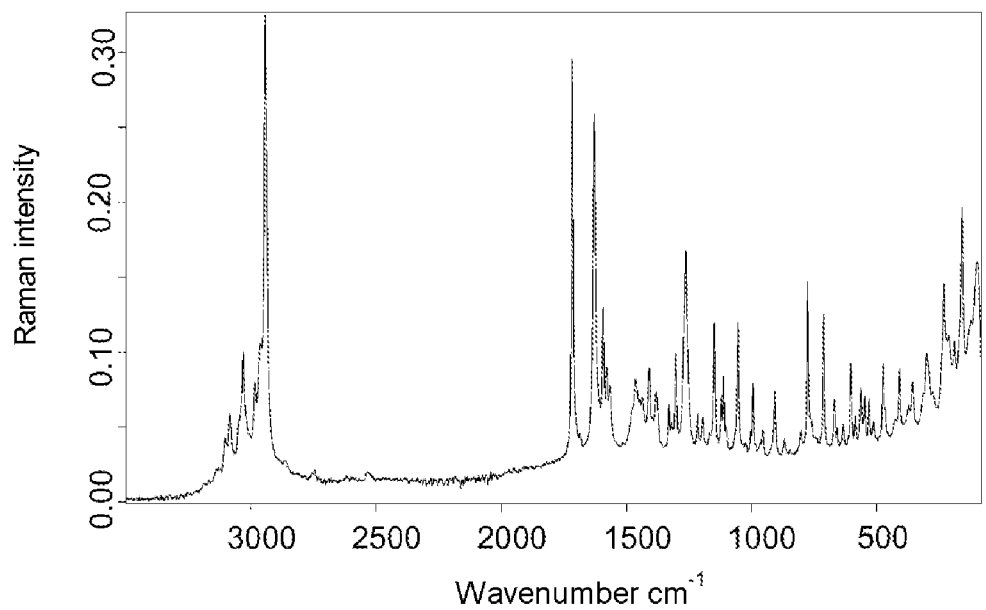

Figure 12: Ramanspectrum of modification "E"
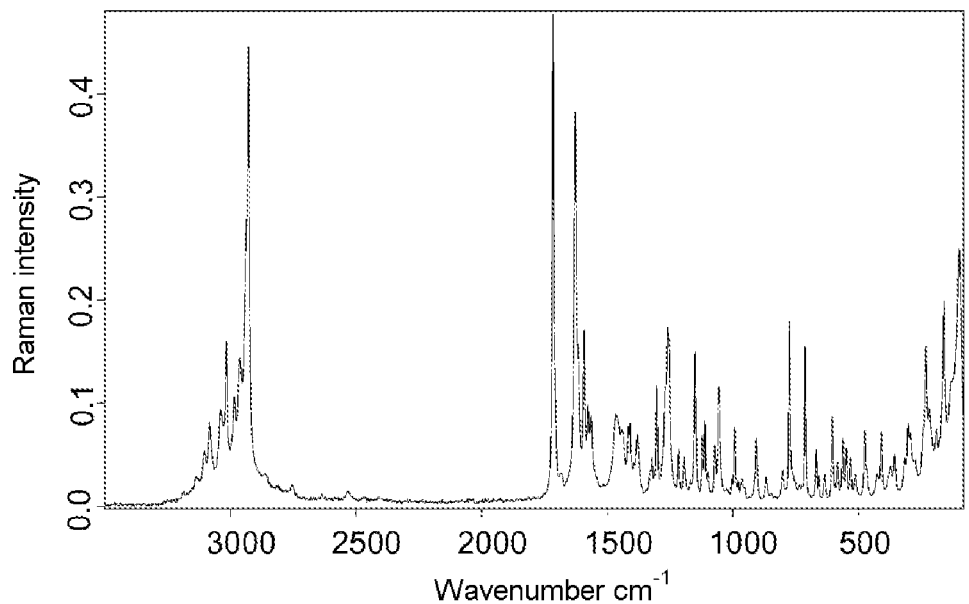
Figure 13: Ramanspectrum of modification "F"
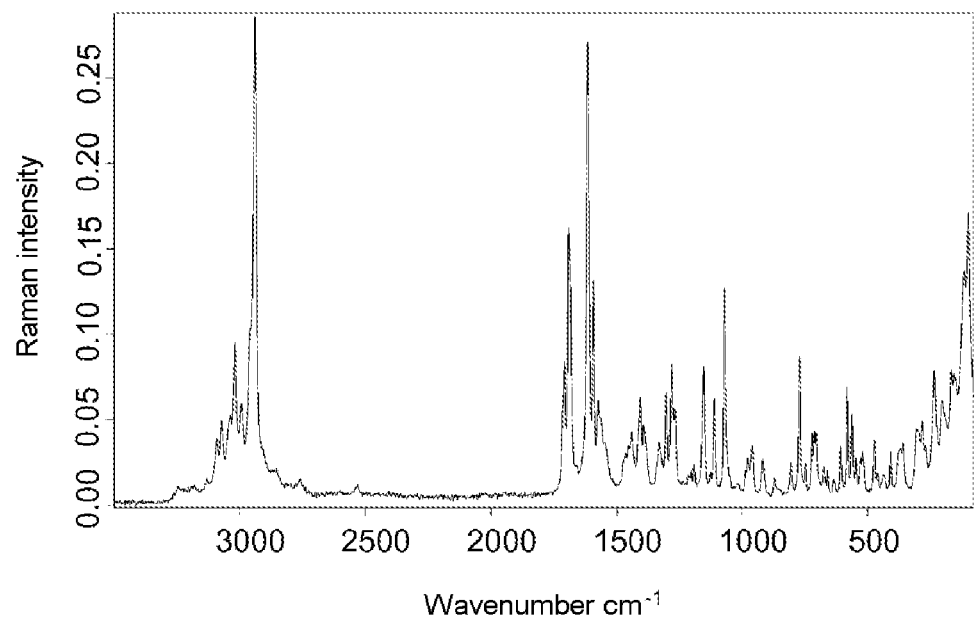

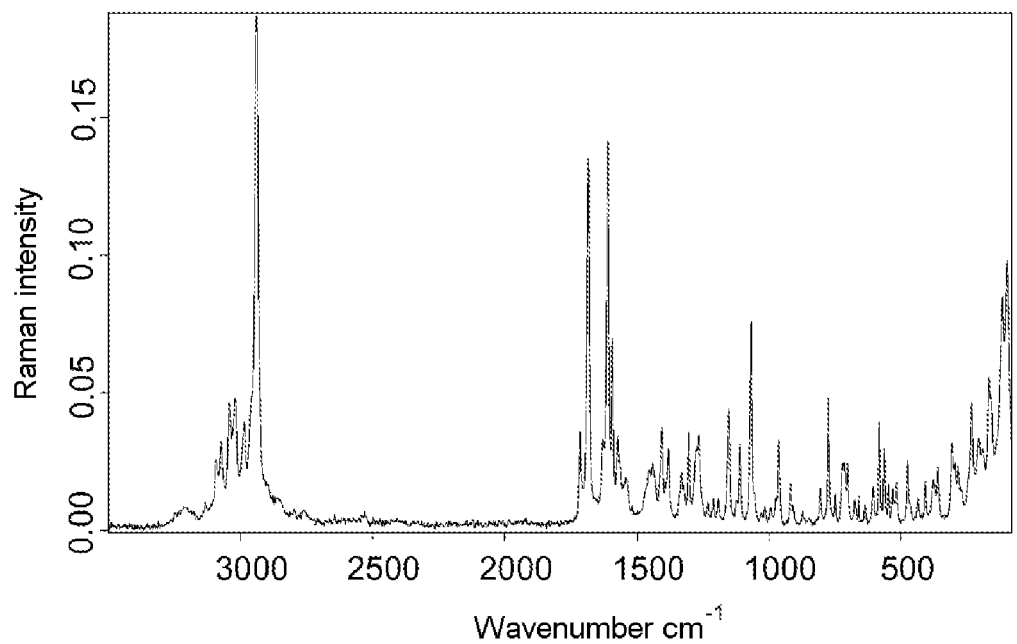
Figure 14: Ramanspectrum of modification "G"

THERMODYNAMICALLY STABLE CRYSTAL MODIFICATION OF 2-METHYL-N-(5-METHYL-1,3,4-OXADIAZOL-2-YL)-3-(METHYLSULFONYL)-4-(TRIFLUOROMETHYL)BENZAMIDE

CROSS-REFERENCE TO RELATED APPLICATIONS

This application is a National Stage entry of International Application No. PCT/EP2016/076620, filed Nov. 4, 2016, which claims priority to European Patent Application No. 15193615.0, filed Nov. 9, 2015.

BACKGROUND

Field

The invention relates to the technical field of crop protection compositions.

It specifically relates to various crystal modifications, in particular the thermodynamically stable crystal modifications of 2-methyl-N-(5-methyl-1,3,4-oxadiazol-2-yl)-3-(methylsulfonyl)-4-(trifluoromethyl)benzamide of the formula (I)

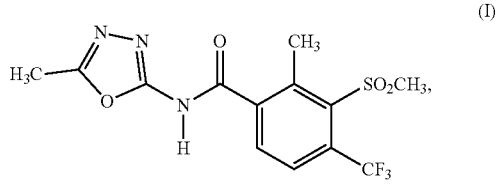 [SMILES: "(I)" ; Cc1nnc(NC(=O)c2ccc(C(F)(F)F)c(S(C)(=O)=O)c2C)o1]

and to methods for the preparation thereof and use thereof as a herbicide. The compound of the formula (I) is referred to below as "benzamide" irrespective of its particular manifestation.

Description of Related Art

It is known that some organic compounds can occur in only one crystal structure, while others, so-called polymorphs, can occur in various crystal structures, see, for example, J. Bernstein, R. J. Davey, J. O. Henck, Angew. Chem. Int. Ed., 1999, 38, 3440-3461. For instance, two crystal structures of the herbicidally active ingredient sulcotrione are known from EP 1 314 724 A1.

The benzamide known for example from WO 2012/126932 A1 (example No. 2-145 in table 2 therein) has herbicidal properties and is suitable for the production of crop protection compositions which can be employed for weed control. However, it has been shown that the benzamide obtainable according to the disclosure of WO 2012/126932 A1 is not suitable for the preparation of user-friendly administration forms. User-friendly administration forms are, for example, suspension formulations in which the benzamide is present finely ground in solid form. Testing in practice has shown that the benzamide obtainable according to the disclosure of WO 2012/126932 A1 leads to crystal growth in suspension formulations and consequently to clumping and precipitation, so that the suspension formulation becomes unusable. The crystal growth can occur spontaneously or over a longer period and cannot be predicted.

SUMMARY

It is therefore an object of the present invention to provide a modification of the benzamide which overcomes these disadvantages and is suitable for the preparation of a suspension formulation which is storage-stable over a prolonged period.

It has been found in the context of the present invention that the benzamide occurs in seven crystal modifications, of which one can be considered as the thermodynamically stable or most stable.

In the context of the present invention, it has also been found that in particular the thermodynamically stable crystal modification of the benzamide does not have the abovementioned disadvantages and therefore is particularly suitable for the preparation of suspension formulations such as suspoconcentrates, suspoemulsions and oil dispersions.

Moreover, the benzamide obtainable according to the disclosure of WO 2012/126932 A1 has the disadvantage that it can be less readily worked up, filtered, purified and wetted with solvents. The poorer wettability is particularly observed in solvents such as water and aqueous solvents and the preparation of suspension formulations is therefore difficult. These disadvantages are overcome by the provision of the thermodynamically stable benzamide according to the invention.

The invention therefore relates to a thermodynamically stable crystal modification of the benzamide 2-methyl-N-(5-methyl-1,3,4-oxadiazol-2-yl)-3-(methylsulfonyl)-4-(trifluoromethyl)benzamide.

In the following, the thermodynamically stable crystal modification of the according to the invention is referred to as crystal modification "A" and the others as crystal modifications "B", "C", "D", "E", "F" and "G".

In the following, the terms "modification" and "crystal modification" are to be understood as equivalent.

X-ray powder diffractometry shows characteristic peaks for each of the crystal modifications, which are reported in Table 1 (crystal modification "A"), Table 2 (crystal modifications "B", "C" and "D") and Table 3 (crystal modifications "E", "F" and "G").

TABLE 1

X-ray powder diffractometry pattern of crystal modification A
Peak maximum [2 theta]
Modification A

| | | |
|---|---|---|
| 9.2 | 23.0 | 30.6 |
| 10.4 | 23.4 | 31.6 |
| 11.4 | 23.9 | 32.3 |
| 12.4 | 24.9 | 32.8 |
| 12.6 | 25.4 | 33.7 |
| 14.0 | 25.7 | 33.9 |
| 17.5 | 25.7 | 34.4 |
| 17.7 | 26.4 | 35.0 |
| 17.9 | 27.2 | 35.1 |
| 18.3 | 27.3 | 35.6 |
| 19.3 | 27.8 | 35.8 |
| 20.1 | 28.0 | 36.2 |
| 20.6 | 28.6 | 36.7 |
| 21.2 | 29.4 | 36.8 |
| 21.8 | 29.6 | 37.3 |
| 22.3 | 29.8 | 37.6 |
| 22.8 | 30.3 | 37.8 |

TABLE 2

X-ray powder diffractometry pattern
of crystal modifications B, C and D
Peak maximum [2 theta]

| Modification B | Modification C | Modification D |
|---|---|---|
| 7.4 | 2.1 | 7.9 |
| 9.7 | 4.2 | 10.0 |

TABLE 2-continued

X-ray powder diffractometry pattern
of crystal modifications B, C and D
Peak maximum [2 theta]

| Modification B | Modification C | Modification D |
|---|---|---|
| 12.6 | 5.1 | 12.5 |
| 13.6 | 6.1 | 13.1 |
| 14.7 | 8.4 | 13.4 |
| 14.9 | 10.1 | 14.8 |
| 16.0 | 10.8 | 15.8 |
| 16.2 | 12.0 | 17.0 |
| 17.5 | 12.3 | 18.7 |
| 18.8 | 12.7 | 19.2 |
| 19.4 | 13.4 | 20.0 |
| 20.5 | 13.6 | 20.2 |
| 21.5 | 15.2 | 20.5 |
| 21.8 | 15.4 | 21.0 |
| 21.9 | 15.6 | 21.5 |
| 22.2 | 16.2 | 22.5 |
| 22.6 | 16.8 | 22.7 |
| 23.1 | 17.1 | 23.0 |
| 23.3 | 17.6 | 23.4 |
| 24.1 | 18.8 | 23.4 |
| 24.2 | 19.0 | 23.7 |
| 25.2 | 19.4 | 24.1 |
| 25.6 | 20.0 | 24.6 |
| 25.8 | 20.2 | 24.9 |
| 26.1 | 20.5 | 25.2 |
| 26.5 | 20.8 | 25.8 |
| 26.8 | 21.5 | 26.6 |
| 27.1 | 21.8 | 27.0 |
| 27.5 | 22.2 | 27.6 |
| 27.6 | 22.3 | 27.8 |
| 28.2 | 23.0 | 28.5 |
| 28.4 | 23.4 | 29.0 |
| 28.7 | 23.7 | 29.5 |
| 29.5 | 24.0 | 30.5 |
| 29.6 | 24.1 | 31.6 |
| 30.5 | 24.6 | 31.8 |
| 31.1 | 25.0 | 32.6 |
| 31.6 | 25.4 | 33.5 |
| 31.8 | 25.5 | 33.8 |
| 32.3 | 25.6 | 34.3 |
| 32.5 | 25.8 | 35.1 |
| 32.8 | 26.1 | 35.5 |
| 33.3 | 26.4 | 36.6 |
| 34.0 | 26.7 | 37.0 |
| 35.4 | 27.3 | |
| 35.9 | 27.7 | |
| 36.7 | 28.1 | |
| 37.1 | 28.5 | |
| | 28.8 | |
| | 29.3 | |
| | 29.7 | |
| | 29.8 | |
| | 30.0 | |
| | 30.6 | |
| | 30.9 | |
| | 31.5 | |
| | 32.2 | |
| | 32.6 | |
| | 33.2 | |
| | 33.5 | |
| | 33.8 | |
| | 34.0 | |
| | 34.5 | |
| | 35.4 | |
| | 36.2 | |
| | 36.8 | |
| | 37.2 | |

TABLE 3

X-ray powder diffractometry pattern of
crystal modifications E, F and G
Peak maximum [2 theta]

| Modification E | Modification F | Modification G |
|---|---|---|
| 6.7 | 4.1 | 2.1 |
| 7.4 | 5.0 | 8.4 |
| 7.9 | 6.1 | 10.1 |
| 8.4 | 7.4 | 12.3 |
| 10.1 | 8.4 | 12.7 |
| 12.5 | 10.7 | 13.1 |
| 12.7 | 11.7 | 13.4 |
| 13.1 | 12.0 | 13.7 |
| 13.4 | 12.3 | 14.6 |
| 13.6 | 12.6 | 15.7 |
| 14.6 | 13.3 | 16.2 |
| 14.8 | 14.6 | 16.9 |
| 15.6 | 15.6 | 17.1 |
| 15.9 | 16.8 | 17.5 |
| 16.0 | 17.7 | 17.7 |
| 16.2 | 18.8 | 17.9 |
| 17.1 | 19.0 | 18.8 |
| 17.3 | 19.4 | 18.9 |
| 17.5 | 20.0 | 19.4 |
| 18.7 | 20.2 | 19.5 |
| 18.8 | 20.5 | 20.4 |
| 19.2 | 21.5 | 20.5 |
| 19.4 | 21.8 | 21.5 |
| 20.1 | 22.1 | 21.8 |
| 20.5 | 22.4 | 22.0 |
| 21.3 | 23.4 | 22.5 |
| 21.5 | 23.7 | 23.3 |
| 21.8 | 24.0 | 23.4 |
| 21.9 | 25.0 | 23.8 |
| 22.2 | 25.3 | 24.2 |
| 22.5 | 25.6 | 25.2 |
| 22.9 | 27.4 | 25.4 |
| 23.1 | 28.2 | 25.6 |
| 23.3 | 29.3 | 25.7 |
| 23.5 | 30.0 | 25.8 |
| 23.9 | 30.9 | 26.1 |
| 24.2 | 31.5 | 27.5 |
| 24.7 | 34.0 | 28.2 |
| 25.2 | 35.4 | 28.9 |
| 25.6 | 36.7 | 30.1 |
| 25.8 | 37.2 | 31.1 |
| 26.1 | | 31.7 |
| 26.4 | | 32.5 |
| 26.9 | | 32.9 |
| 26.9 | | 34.0 |
| 27.2 | | 34.5 |
| 27.5 | | 35.5 |
| 27.6 | | 35.8 |
| 27.8 | | 37.4 |
| 28.1 | | |
| 28.6 | | |
| 29.2 | | |
| 29.6 | | |
| 29.8 | | |
| 30.2 | | |
| 30.5 | | |
| 31.1 | | |
| 31.5 | | |
| 31.8 | | |
| 32.3 | | |
| 32.5 | | |
| 32.9 | | |
| 33.1 | | |
| 33.3 | | |
| 33.7 | | |
| 34.0 | | |
| 34.4 | | |
| 35.4 | | |
| 35.9 | | |
| 37.1 | | |
| 37.5 | | |
| 37.9 | | |

Measurement Conditions:

| | |
|---|---|
| Anode material | Cu |
| K-alpha1 [Å] | 1.54060 |
| Generator setting | 40 mA, 40 kV |
| Primary beam monochromator | focusing X-ray mirror |
| Sample rotation | yes |
| Scan axis | Gonio |
| Start position [°2 Th.] | 2.0066 |
| End position [°2 Th.] | 37.9906 |

BRIEF DESCRIPTION OF THE DRAWINGS

The corresponding X-ray diffractograms of crystal modifications A to G are shown in FIGS. 1 to 7.

DETAILED DESCRIPTION OF A PREFERRED EMBODIMENT

The single crystal X-ray structure analysis was determined by using a rotary anode M18X-HF with MoKα radiation from MACScience Co and a Bruker AXS SMART CCD 1000 detector. The data were processed with the programs SAINT-NT V 5.0 (data reduction, Bruker AXS) and SADABS (absorption correction, Bruker AXS). Structure solution and refinement was performed with SHELXTL-NT Version V5.1.

Raman spectroscopy reveals a characteristic Raman spectrum for each of the crystal modifications, which are shown in FIGS. 8 to 14, and characteristic band maxima, which are reported in Table 4 (crystal modification "A"), Table 5 (crystal modifications "B", "C" and "D") and Table 6 (crystal modifications "E", "F" and "G").

TABLE 4

Band maxima of Raman spectra patterns
of crystal modification A
Band maximum [cm$^{-1}$]
Modification A

| | | |
|---|---|---|
| 3080 | 1267 | 603 |
| 3066 | 1214 | 584 |
| 3039 | 1194 | 566 |
| 3030 | 1156 | 544 |
| 3009 | 1148 | 530 |
| 2948 | 1136 | 508 |
| 2928 | 1109 | 477 |
| 1719 | 1066 | 469 |
| 1681 | 1010 | 428 |
| 1618 | 965 | 404 |
| 1592 | 957 | 382 |
| 1577 | 909 | 359 |
| 1563 | 868 | 303 |
| 1545 | 803 | 288 |
| 1445 | 772 | 270 |
| 1412 | 758 | 231 |
| 1404 | 746 | 186 |
| 1391 | 720 | 154 |
| 1330 | 710 | 143 |
| 1303 | 672 | 105 |

TABLE 5

Band maxima of Raman spectra patterns of
crystal modifications B, C and D
Band maximum [cm$^{-1}$]

| Modification B | Modification C | Modification D |
|---|---|---|
| 3091 | 3100 | 3104 |
| 3074 | 3068 | 3084 |
| 3044 | 3052 | 3030 |
| 3018 | 3019 | 2984 |
| 2995 | 2994 | 2962 |
| 2946 | 2960 | 2944 |
| 2934 | 2940 | 2745 |
| 2869 | 2914 | 1718 |
| 2764 | 1710 | 1687 |
| 1710 | 1694 | 1630 |
| 1617 | 1666 | 1594 |
| 1594 | 1619 | 1580 |
| 1563 | 1594 | 1567 |
| 1551 | 1576 | 1464 |
| 1454 | 1564 | 1447 |
| 1446 | 1464 | 1437 |
| 1405 | 1438 | 1408 |
| 1394 | 1404 | 1380 |
| 1390 | 1386 | 1329 |
| 1323 | 1332 | 1302 |
| 1302 | 1304 | 1262 |
| 1280 | 1281 | 1215 |
| 1267 | 1265 | 1194 |
| 1217 | 1203 | 1148 |
| 1189 | 1152 | 1121 |
| 1173 | 1112 | 1111 |
| 1155 | 1072 | 1101 |
| 1113 | 1059 | 1054 |
| 1072 | 978 | 994 |
| 1048 | 959 | 955 |
| 1020 | 921 | 907 |
| 979 | 873 | 868 |
| 959 | 856 | 803 |
| 911 | 808 | 775 |
| 866 | 771 | 711 |
| 803 | 747 | 668 |
| 773 | 713 | 658 |
| 750 | 705 | 633 |
| 726 | 669 | 603 |
| 711 | 661 | 584 |
| 674 | 631 | 562 |
| 657 | 607 | 547 |
| 639 | 581 | 530 |
| 608 | 563 | 512 |
| 582 | 548 | 474 |
| 561 | 523 | 423 |
| 549 | 473 | 407 |
| 530 | 444 | 371 |
| 515 | 409 | 356 |
| 475 | 368 | 300 |
| 461 | 360 | 230 |
| 431 | 313 | 212 |
| 410 | 300 | 189 |
| 366 | 284 | 159 |
| 301 | 271 | 123 |
| 284 | 237 | 98 |
| 266 | 225 | |
| 243 | 202 | |
| 233 | 187 | |
| 206 | 166 | |
| 176 | 149 | |
| 156 | 115 | |
| 127 | | |
| 100 | | |

TABLE 6

Band maxima of Raman spectra patterns
of crystal modifications E, F and G
Band maximum [cm⁻¹]

| Modification E | Modification F | Modification G |
|---|---|---|
| 3135 | 3091 | 3208 |
| 3103 | 3073 | 3134 |
| 3083 | 3037 | 3092 |
| 3039 | 3019 | 3074 |
| 3016 | 2994 | 3044 |
| 2984 | 2940 | 3019 |
| 2962 | 2756 | 2987 |
| 2935 | 2530 | 2940 |
| 2928 | 1710 | 1718 |
| 1718 | 1693 | 1686 |
| 1687 | 1617 | 1630 |
| 1630 | 1594 | 1612 |
| 1594 | 1576 | 1594 |
| 1579 | 1551 | 1575 |
| 1566 | 1466 | 1544 |
| 1467 | 1454 | 1454 |
| 1444 | 1440 | 1442 |
| 1418 | 1406 | 1407 |
| 1412 | 1392 | 1392 |
| 1382 | 1331 | 1383 |
| 1322 | 1303 | 1331 |
| 1303 | 1280 | 1303 |
| 1259 | 1267 | 1267 |
| 1215 | 1192 | 1331 |
| 1194 | 1153 | 1210 |
| 1150 | 1125 | 1192 |
| 1122 | 1112 | 1152 |
| 1112 | 1071 | 1123 |
| 1072 | 960 | 1110 |
| 1055 | 918 | 1066 |
| 994 | 872 | 1029 |
| 979 | 806 | 1015 |
| 963 | 772 | 992 |
| 906 | 748 | 962 |
| 868 | 721 | 916 |
| 802 | 711 | 872 |
| 775 | 705 | 805 |
| 711 | 675 | 775 |
| 668 | 660 | 748 |
| 658 | 636 | 716 |
| 634 | 607 | 702 |
| 604 | 582 | 675 |
| 584 | 563 | 659 |
| 561 | 548 | 637 |
| 548 | 529 | 606 |
| 531 | 521 | 582 |
| 512 | 474 | 563 |
| 475 | 461 | 547 |
| 425 | 436 | 530 |
| 409 | 409 | 519 |
| 372 | 370 | 475 |
| 356 | 359 | 436 |
| 315 | 306 | 408 |
| 302 | 283 | 377 |
| 293 | 271 | 361 |
| 274 | 234 | 307 |
| 232 | 205 | 296 |
| 218 | 168 | 283 |
| 189 | 156 | 232 |
| 160 | 116 | 205 |
| 125 | 100 | 191 |
| 100 |  | 167 |
|  |  | 160 |
|  |  | 115 |
|  |  | 98 |

Measurement Conditions:

| Instrument | Bruker Raman RFS 100/S and/or Bruker Multiram |
|---|---|
| Number of scans | 64 |
| Resolution | 2-4 cm⁻¹ |
| Laser power | 50 mW |
| Laser wavelength | 1064 nm |

The benzamide of the formula (I) can be prepared per se by one of the methods described in WO 2012/126932 A1 for example. Depending on the type of solvent used in the final purification step and the temperature regime, the benzamide is usually obtained in amorphous form, in the form of one of the crystal modifications B to G described here or in a mixture of the amorphous form and the crystal modifications B to G.

The thermodynamically stable crystal modification A of the benzamide may be prepared for example in a general manner such that the benzamide obtainable according to WO 2012/126932 A1 is suspended and/or dissolved in a suitable solvent and treated at temperatures of 0° C. up to the boiling point of the solvent until quantitative conversion into the thermodynamically stable crystal modification A.

The invention therefore further relates to a method for preparing the thermodynamically stable crystal modification A of the benzamide, wherein crystal modifications B to G of the benzamide are suspended and/or dissolved in solvents and treated at temperatures of 0° C. up to the boiling point of the solvent until quantitative conversion into the thermodynamically stable crystal modification A.

Suitable solvents for use in this process are, for example, lower alcohols such as methanol, ethanol, 2-propanol, or ketones such as acetone, 2-butanone, which can also be used in a mixture with water. Lower alcohols or ketones refer here to those compounds which have one to ten carbon atoms, preferably one to five carbon atoms. Further suitable solvents are benzene, toluene and chlorobenzene. Preference is given to toluene and mixtures of ethanol and water, particularly preferably toluene and a mixture of ethanol and water in the ratio 1:1.

The conversion to the thermodynamically stable crystal modification A is effected at temperatures less than 100° C., preferably at temperatures of 0° C. to 80° C., particularly preferably at temperatures of 20° C. to 80° C., especially preferably at temperatures of 20° C. to 40° C. The duration of the conversion depends on the temperature and type of solvent. In addition, the duration of the conversion depends on whether seed crystals of the crystal modification A are used. In general, the conversion to crystal modification A can be achieved directly, on complete dissolution of the crystals of crystal modifications B to G at elevated temperature, by cooling crystallization to room temperature, without using seed crystals. The cooling to room temperature is effected preferably with a cooling rate of less than 25° C., particularly preferably with a cooling rate of less than 20° C. The conversion to a suspension of crystal modification A can generally be brought about without the use of seed crystals within a period of 14 days. When seed crystals of crystal modification A are used in the conversion of a suspension, a treatment time of 24 to 48 hours is generally sufficient in order to achieve a quantitative conversion of the crystals to the crystal modification A.

The resulting crystals of crystal modification A are finally separated off and are dried to constant weight by removing the solvent at room temperature or elevated temperature.

The stable crystal modification A can also be obtained from the crystal modifications B to G or the amorphous form by grinding under high pressure. A suitable pressure is a pressure of at least 5 bar.

Crystal modification A, by virtue of its stability, is outstandingly suitable for the preparation of formulations, especially suspension formulations, of crop protection compositions. Accordingly, the invention also provides crop protection compositions comprising crystal modification A of the benzamide alone or as a mixture with auxiliaries and carriers, and also as a mixture with other active ingredients. The invention also includes mixtures of crystal modification A of the benzamide with crystal modifications B to G of the benzamide, for example those which arise at any point during the conversion process according to the invention of crystal modifications B to G I into crystal modification A. Preference is given to an active ingredient quality with more than 80% by weight of crystal modification A of the benzamide, particularly preferably with more than 90% by weight, especially preferably with more than 95% by weight and most preferably with more than 98% by weight.

The benzamide of the stable crystal modification A is optionally mixed with one or more other herbicides. Such mixtures also profit from the advantageous properties of the inventive crystal modification A.

Owing to its stability, the stable crystal modification A of the benzamide is suitable in general terms for use as starting material for the preparation of any plant protection formulations comprising this benzamide, even when the benzamide is no longer in this form following formulation but, say in dissolved form.

The invention therefore also provides methods for preparing the plant protection formulations comprising the benzamide which employ the stable crystal modification A of the benzamide and also plant protection formulations comprising this benzamide which were obtained from the stable crystal modification A of the benzamide. Using the stable crystal modification A enhances consistency for benzamide preparations and therefore the risk of incorrect dosages decreases.

The stable crystal modification A of the benzamide can be converted in a known manner to the customary formulations, such as suspension concentrates, colloidal concentrates, dispersible concentrates, emulsifiable concentrates (emulsion concentrates), seed-dressing emulsions, seed-dressing suspensions, granules, microgranules, suspoemulsions, oil dispersions, water-soluble granules, water-soluble concentrates and water-dispersible granules, using suitable auxiliaries and carriers or solvents. In this connection, the active ingredient should be present at a concentration of approximately 0.5 to 90% by weight of the total mixture, i.e. in amounts which are sufficient in order to achieve the dosage level required. The formulations are prepared, for example, by extending the stable crystal modification A of the benzamide with solvents and/or carriers, optionally using emulsifiers and/or dispersants, and/or other auxiliaries, for example penetrants.

Application is effected in a customary manner, by contacting the unwanted plants and/or their habitat with the active ingredient or formulations thereof.

Moreover, the thermodynamically stable crystal modification A of the benzamide can be very readily processed, filtered and purified.

The benzamide in the stable crystal modification A exhibits an excellent herbicidal activity on representatives of the group both of monocotyledonous and dicotyledonous plants. Examples here include:

Dicotyledonous plants of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Monocotyledonous plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

The invention therefore also relates to the use of the stable crystal modification A of the benzamide for preparing a plant protection composition for the treatment of weed infestation.

The stable crystal modification A of the benzamide according to the invention is suitable, owing to its compatibility with crop plants, for controlling unwanted plants in crops of, for example, wheat, barley, oats, rye, rice, maize, sugar beet, sugar cane, cotton and soya, in particular in wheat, barley, oats and rye.

All plants and plant parts can be treated in accordance with the invention. Plants in this context are understood to include all plants and plant populations, such as desired and unwanted wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts are to be understood as meaning all aboveground and below-ground parts and organs of plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example cuttings, tubers, rhizomes, shoots and seeds.

Treatment according to the invention of the plants and plant parts with crystal modification A of the benzamide according to the invention is carried out directly or by exposure to their surroundings, habitat or storage space by the customary treatment methods, for example by immersion, spraying, evaporation, fogging, scattering or painting on.

The crystal modification A of the benzamide according to the invention, as already explained above, may be converted into the customary formulations such as solutions, emulsions, wettable powders, suspensions, powders, dusts, pastes, soluble powders, granules, suspension-emulsion concentrates, natural and synthetic materials impregnated with active ingredient, and microencapsulations in polymeric materials.

These formulations are produced in a known manner, for example by mixing the active compounds with extenders, that is, liquid solvents and/or solid carriers, optionally with the use of surfactants, that is to say, emulsifiers and/or dispersants, and/or foam formers.

When the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are for example nonionogenic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; suitable dispersants are for example lignosulfite waste liquors and methylcellulose.

In the formulations it is possible to use tackifiers such as carboxymethylcellulose, natural and synthetic polymers in the form of powders, granules or latexes, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian blue, and organic colorants such as alizarin colorants, azo-colorants and metal phthalocyanine colorants, and trace nutrients such as salts of iron, manganese, boron, copper, cobalt, molybdenum and zinc.

In general, the formulations comprise between 0.1 and 95 percent by weight of the active ingredient in the form of crystal modification A according to the invention, preferably between 0.5 and 90%.

For controlling weeds, crystal modification A of the benzamide according to the invention, as such or in its formulations, can also be used as mixtures with known herbicides and/or substances which improve compatibility with crop plants ("safeners"), finished formulations or tank mixes being possible. Also possible are mixtures with weedkillers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (—P-ethyl), fentrazamide, flamprop (-isopropyl, -isopropyl-L, -methyl), flazasulfuron, florasulam, fluazifop (—P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flupyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopralin, isoproturon, isouron, isoxaben, isoxachlortole, isoxaflutole, isoxapyrifop, lactofen, lenacil, linuron, MCPA, mecoprop, mefenacet, mesosulfuron (-methyl, -sodium), mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore, known safeners are suitable for the mixtures, for example: AD-67, BAS-145138, benoxacor, cloquintocet (-mexyl), cyometrinil, cyprosulfamide, 2,4-D, DKA-24, dichlormid, dymron, fenclorim, fenchlorazole (-ethyl), flurazole, fluxofenim, furilazole, isoxadifen (-ethyl), MCPA, mecoprop (—P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The crystal modification A of the benzamide according to the invention can be applied as such, in the form of its formulations or in the use forms prepared therefrom by further dilution, such as ready-to-use solutions, suspensions, emulsions, powders, pastes and granules. Application is accomplished in a customary manner, for example by watering, spraying, atomizing or broadcasting.

The crystal modification A of the benzamide according to the invention can be applied both before and after emergence of the plants. It can also be incorporated into the soil before sowing.

The amount of active compound used can vary within a relatively wide range. It depends essentially on the nature of the desired effect. In general, the amounts used are between 1 g and 1 kg of active ingredient per hectare of soil surface, preferably between 5 g and 500 g per ha.

As already mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are to be understood as meaning plants having certain properties ("traits") which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. Thus, for example, reduced application rates and/or a widening of the activity spectrum and/or an increase in the activity of the substances and compositions to be used according to the invention—also in combination with other active agrochemical ingredients-, better crop plant growth, increased tolerance of the crop plants to high or low temperatures, increased tolerance of the crop plants to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are an improved defense of the plants against animal and microbial pests, such as against insects, mites, phytopathogenic fungi, bacteria and/or viruses, and also increased tolerance of the plants to certain herbicidally active compounds. Examples of transgenic plants are the important crop plants, such as cereals (wheat, rice), soya beans, potatoes, cotton, oilseed rape and also in particular maize, and also fruit plants (with the fruits being apples, pears, citrus fruits and grapes), and particular emphasis is given particularly to maize, but also to soya beans, potatoes, cotton and oilseed rape. Traits that are particularly emphasized are the increased defense of the plants against insects, by means of toxins which form in the plants, especially those generated in the plants by the genetic material from Bacillus thuringiensis (e.g. by the genes CryIA(a), CryIA(b), CryIA(c), CryIIA, CryIIIA, CryIIIB2, Cry9c, Cry2Ab, Cry3Bb and CryIF, and also combinations thereof) (hereinafter "Bt plants"). Traits that are also particularly emphasized are the improved defense of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain herbicidally active compounds, for example imidazolinones, sulfonylureas, glyphosate or phosphinothricin (for example the "PAT" gene). The genes which impart the desired properties ("traits") in question may also be present in combinations with one another in the transgenic plants. Examples of "Bt plants" which may be mentioned are particularly maize varieties but also cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants include particularly maize varieties but also cotton varieties and soya bean varieties which are sold under the trade names Roundup Ready® (tolerance to glyphosate e.g. maize, cotton, soya beans), Liberty Link® (tolerance to phosphinothricin, e.g. oilseed rape), IMI® (tolerance to imidazolinones) and STS® (tolerance to sulfonylureas, e.g. maize). Herbicide-resistant plants (bred conventionally for herbicide tolerance) also include the varieties sold under the Clearfield® name (e.g. maize). Of course, these statements also apply to plant cultivars which have these genetic traits or genetic traits which are yet to be developed and will be developed and/or marketed in the future.

WORKING EXAMPLES

Preparation of the Thermodynamically Stable Crystal Modification A 0.1 g of the benzamide prepared in accordance with the methods disclosed in WO 2012/126932 A1 was suspended in 0.5 ml of methanol. The suspension is shaken and left to stand respectively in intervals of 30 minutes each at 25° C. for a total of 168 hours. This affords the benzamide in the thermodynamically stable crystal modification A.

Ab Initio Preparation of the Thermodynamically Stable Crystal Modification A 57 g (200 mmol) of 2-methyl-3-methylsulfonyl-4-trifluoromethylbenzoic acid, 21.8 g (220 mmol) of 2-amino-5-methyl-1,3,4-oxadiazole and 32.8 g (400 mmol) of N-methylimidazole are dissolved in 300 ml of 3-methylpyridine and stirred for 30 minutes. After cooling to 10° C., 38.2 g (320 mmol) of thionyl chloride are added dropwise over 60 minutes such that the temperature remains between 10° C. and 20° C. The reaction mixture was then stirred at 20° C. for another 18 hours. 200 ml of water were added dropwise to the reaction mixture at 25-30° C. over 180 minutes. The suspension was further stirred for 3 hours at 20° C., the product filtered off and washed with 200 ml of water and 100 ml of 5% hydrochloric acid. After drying, 64 g (yield 86%) of the benzamide was obtained in the form of the thermodynamically stable crystal modification A.

In a first comparative experiment, in contrast to other modifications of this compound, the thermodynamically stable crystal modification A already demonstrated 100% wettability after 1 minute on mixing with water.

Ab Initio Preparation of the Thermodynamically Stable Crystal Modification B 57 g (200 mmol) of 2-methyl-3-methylsulfonyl-4-trifluoromethylbenzoic acid, 21.8 g (220 mmol) of 2-amino-5-methyl-1,3,4-oxadiazole and 32.8 g (400 mmol) of N-methylimidazole are dissolved in 300 ml of 3-methylpyridine and stirred for 30 minutes. After cooling to 10° C., 38.2 g (320 mmol) of thionyl chloride are added dropwise over 60 minutes such that the temperature remains between 10° C. and 20° C. The reaction mixture was then stirred at 20° C. for another 18 hours. 200 ml of water were added dropwise to the reaction mixture at 0-5° C. over 30 minutes. The suspension was further stirred for 1 hour at 5° C., the product filtered off and washed with 200 ml of water and 100 ml of 5% hydrochloric acid. After drying, 62 g (yield 85%) of the benzamide was obtained in the form of the crystal modification B.

Preparation of Crystal Modification C 0.1 g of the benzamide prepared in accordance with the methods disclosed in WO 2012/126932 A1 was dissolved in 60 ml of methanol at boiling point. The solution is then left to stand at 23° C. in a crystallizing dish with a watchglass as covering until the solvent is completely evaporated. This affords the benzamide in the crystal modification C.

Preparation of Crystal Modification D 0.1 g of the benzamide prepared according to the methods disclosed in WO 2012/126932 A1 was heated to 230° C. in an unsealed glass vessel and then stored at 150° C. for 24 hours. This affords the benzamide in the crystal modification D.

Preparation of Crystal Modification E 0.1 g of the benzamide prepared in accordance with the methods disclosed in WO 2012/126932 A1 was dissolved in 10 ml of acetone at boiling point. The solution is then left to stand at 23° C. in a crystallizing dish with a watchglass as covering until the solvent is completely evaporated. This affords the benzamide in the crystal modification E.

Preparation of Crystal Modification F 0.1 g of the benzamide prepared in accordance with the methods disclosed in WO 2012/126932 A1 was dissolved in 15 ml of methanol at boiling point. The solution is then left to stand at 5° C. in a crystallizing dish with a watchglass as covering until the solvent is completely evaporated. This affords the benzamide in the crystal modification F.

Preparation of Crystal Modification G 0.1 g of the benzamide prepared in accordance with the methods disclosed in WO 2012/126932 A1 was dissolved in 15 ml of methanol at boiling point. After addition of 50 ml of toluene, the solution is left to stand at 23° C. in a crystallizing dish with a watchglass as covering until the solvent is completely evaporated. This affords the benzamide in the crystal modification G.

Stability Tests

An oil dispersion of the benzamide of the crystal modification A, compared to an oil dispersion of the benzamide prepared according to the methods disclosed in WO 2012/126932 A1, shows no signs of clumping and precipitation even after several weeks of storage.

The invention claimed is:

1. A thermodynamically stable crystal modification A of 2-methyl-N-(5-methyl-1,3,4-oxadiazol-2-yl)-3-(methylsulfonyl)-4-(trifluoromethyl)benzamide, wherein the crystal modification a) has an X-ray powder diffractometry pattern with the following peaks, measured at a copper anode at a K-alpha1 radiation of 1.54060 Ångstrom, specified in degrees 2 theta:

| | | |
|---|---|---|
| 9.2 | 23.0 | 30.6 |
| 10.4 | 23.4 | 31.6 |
| 11.4 | 23.9 | 32.3 |
| 12.4 | 24.9 | 32.8 |
| 12.6 | 25.4 | 33.7 |
| 14.0 | 25.7 | 33.9 |
| 17.5 | 25.7 | 34.4 |
| 17.7 | 26.4 | 35.0 |
| 17.9 | 27.2 | 35.1 |
| 18.3 | 27.3 | 35.6 |
| 19.3 | 27.8 | 35.8 |
| 20.1 | 28.0 | 36.2 |
| 20.6 | 28.6 | 36.7 |
| 21.2 | 29.4 | 36.8 |
| 21.8 | 29.6 | 37.3 |
| 22.3 | 29.8 | 37.6 |
| 22.8 | 30.3 | 37.8 | and b) has a Raman spectrum with band maxima specified in [cm$^{-1}$], of:

| | | |
|---|---|---|
| 3080 | 1267 | 603 |
| 3066 | 1214 | 584 |
| 3039 | 1194 | 566 |
| 3030 | 1156 | 544 |
| 3009 | 1148 | 530 |
| 2948 | 1136 | 508 |
| 2928 | 1109 | 477 |
| 1719 | 1066 | 469 |
| 1681 | 1010 | 428 |
| 1618 | 965 | 404 |
| 1592 | 957 | 382 |
| 1577 | 909 | 359 |
| 1563 | 868 | 303 |
| 1545 | 803 | 288 |
| 1445 | 772 | 270 |
| 1412 | 758 | 231 |
| 1404 | 746 | 186 |
| 1391 | 720 | 154 |
| 1330 | 710 | 143 |
| 1303 | 672 | 105. |

2. A herbicidal composition comprising a content of the thermodynamically stable crystal modification A of 2-methyl-N-(5-methyl-1,3,4-oxadiazol-2-yl)-3-(methylsulfonyl)-4-(trifluoromethyl)benzamide as claimed in claim 1 and one or more standard extenders and/or surface-active auxiliaries.

3. The herbicidal composition as claimed in claim 2, wherein the 2-methyl-N-(5-methyl-1,3,4-oxadiazol-2-yl)-3-(methylsulfonyl)-4-(trifluoromethyl)benzamide is present to an extent of more than 90% by weight in the stable crystal modification A.

4. The herbicidal composition as claimed in claim 3, wherein the 2-methyl-N-(5-methyl-1,3,4-oxadiazol-2-yl)-3-(methylsulfonyl)-4-(trifluoromethyl)benzamide is present to an extent of more than 95% by weight in the stable crystal modification A.

5. The herbicidal composition comprising the thermodynamically stable crystal modification A of 2-methyl-N-(5-methyl-1,3,4-oxadiazol-2-yl)-3-(methylsulfonyl)-4-(trifluoromethyl)benzamide as claimed in claim 1 and a metastable crystal modification, wherein the 2-methyl-N-(5-methyl-1,3,4-oxadiazol-2-yl)-3-(methylsulfonyl)-4-(trifluoromethyl)benzamide is present to an extent of more than 90% by weight in the stable crystal modification A.

6. The herbicidal composition as claimed in claim 5, wherein the 2-methyl-N-(5-methyl-1,3,4-oxadiazol-2-yl)-3-(methyl sulfonyl)-4-(trifluoromethyl)benzamide is present to an extent of more than 95% by weight in the stable crystal modification A.

7. The herbicidal composition as claimed in claim 4, wherein the 2-methyl-N-(5-methyl-1,3,4-oxadiazol-2-yl)-3-(methylsulfonyl)-4-(trifluoromethyl)benzamide is present to an extent of more than 98% by weight in the stable crystal modification A.

8. A product comprising the thermodynamically stable crystal modification A of 2-methyl-N-(5-methyl-1,3,4-oxadiazol-2-yl)-3-(methylsulfonyl)-4-(trifluoromethyl)benzamide as claimed in claim 1 or a composition thereof for controlling unwanted plants.

9. A method for controlling one or more unwanted plants, comprising allowing the thermodynamically stable crystal modification A as claimed in claim 1 or a composition thereof to act on the unwanted plants and/or a habitat thereof.

10. The method as claimed in claim 9 for controlling harmful plants in monocotyledonous plant crops.

11. The method as claimed in claim 9 in which the plant crops are genetically modified or have been obtained by mutation-selection.

* * * * *